United States Patent [19]
Feingold

[11] Patent Number: 5,941,886
[45] Date of Patent: *Aug. 24, 1999

[54] HINGELESS LENS CARTRIDGES FOR INSERTION OF DEFORMABLE INTRAOCULAR LENS

[75] Inventor: Vladimir Feingold, Laguna Niguel, Calif.

[73] Assignee: Staar Surgical Company, Inc., Monrovia, Calif.

[*] Notice: This patent is subject to a terminal disclaimer.

[21] Appl. No.: 08/196,855

[22] Filed: Feb. 15, 1994

Related U.S. Application Data

[63] Continuation-in-part of application No. 07/953,251, Sep. 30, 1992, abandoned.

[51] Int. Cl.$^6$ .................................................. A61F 9/00
[52] U.S. Cl. .................................................. 606/107; 623/6
[58] Field of Search .................... 606/107; 623/6; 206/5.1

[56] References Cited

U.S. PATENT DOCUMENTS

| | | | |
|---|---|---|---|
| 4,681,102 | 7/1987 | Bartell | 623/6 X |
| 4,702,244 | 10/1987 | Mazzocco | 623/6 X |
| 4,781,719 | 11/1988 | Kelman | 623/6 |
| 4,919,130 | 4/1990 | Stoy et al. | |
| 4,934,363 | 6/1990 | Smith et al. | 623/6 X |
| 5,123,905 | 6/1992 | Kelman | |
| 5,190,552 | 3/1993 | Kelman | |
| 5,275,604 | 1/1994 | Rheinish et al. | 606/107 |
| 5,474,562 | 12/1995 | Orchowski et al. | 606/107 |

OTHER PUBLICATIONS

One (1) sheet of drawings of prior art device sold by Staar Surgical Company of Monrovia, CA.

International application No. PCT/US93/09255 and related International Search Report published on Apr. 14, 1994 based on U.S. Patent application serial No. 07/953,251.

*Primary Examiner*—Michael Buiz
*Assistant Examiner*—Kevin Truong
*Attorney, Agent, or Firm*—Klima & Pezzlo, P.C.

[57] ABSTRACT

A hingeless type intraocular lens microcartridge for use with a surgical insertion instrument. The hingeless microcartridge has a fixed configuration with a transition portion extending between a lens receiving portion and a nozzle portion.

77 Claims, 10 Drawing Sheets

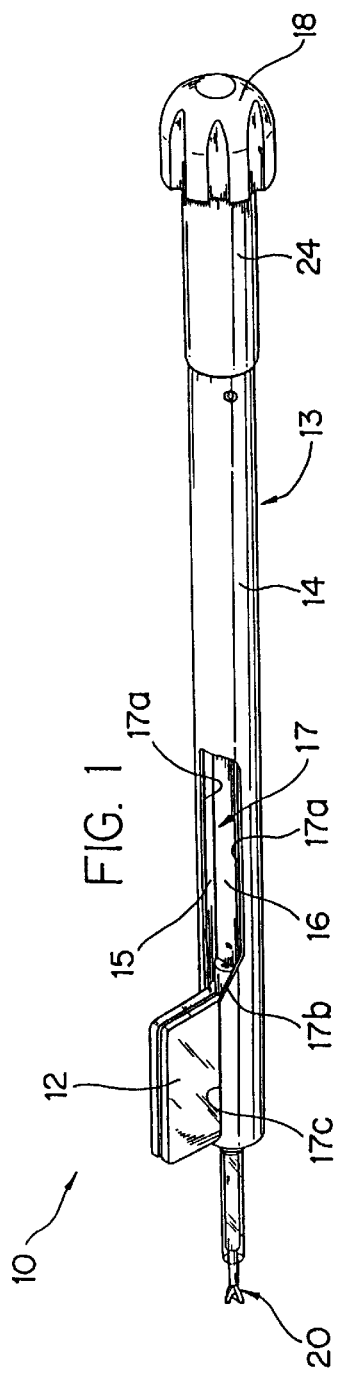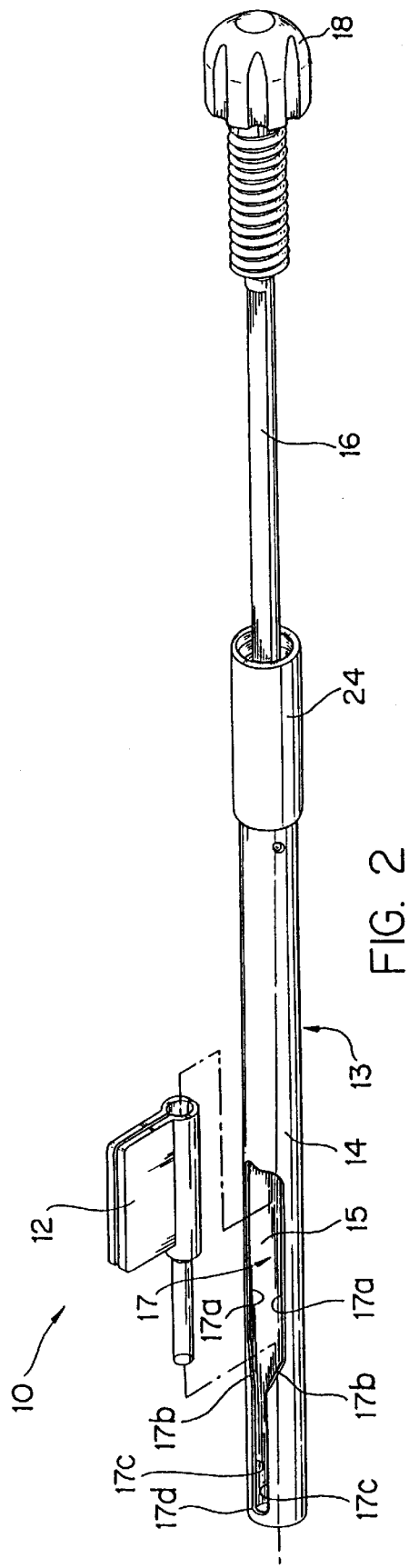

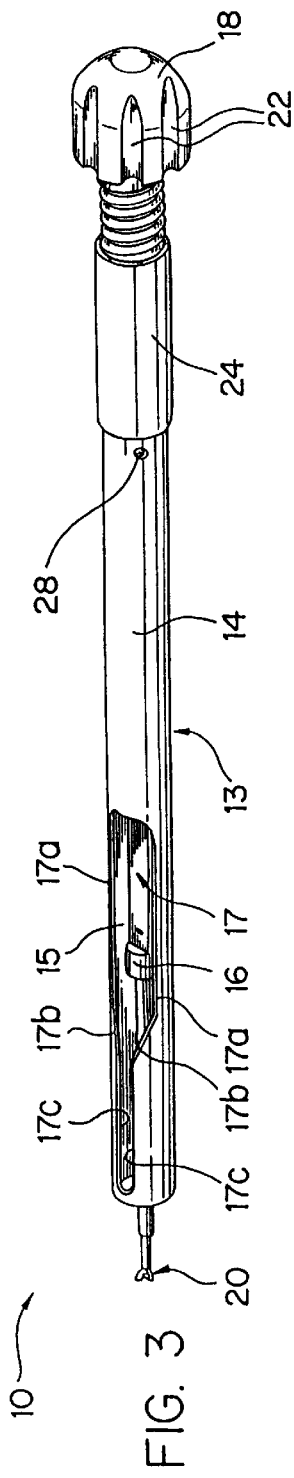
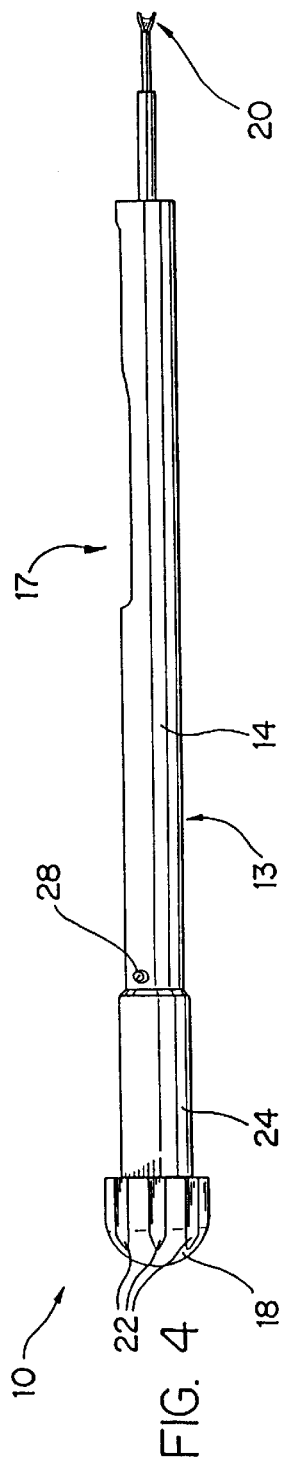
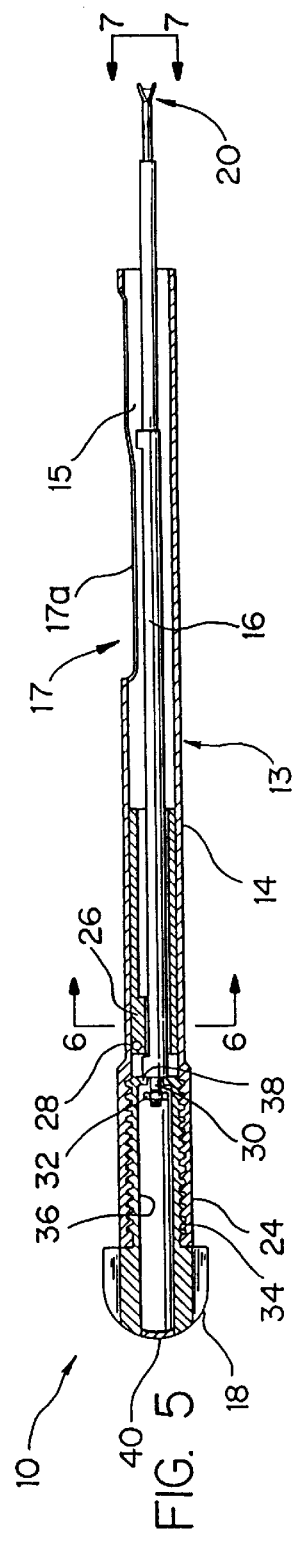

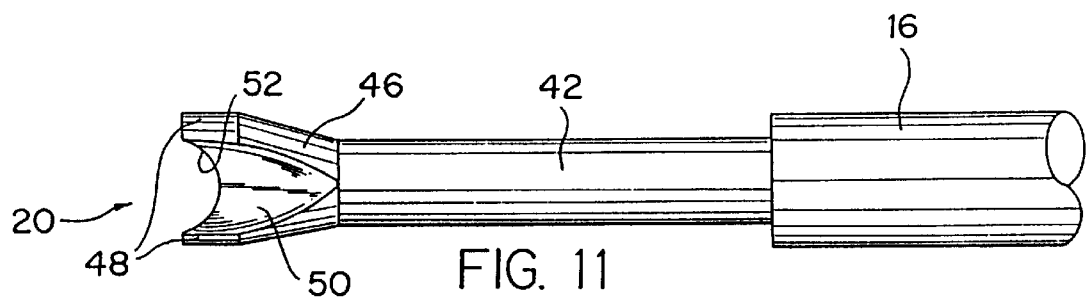
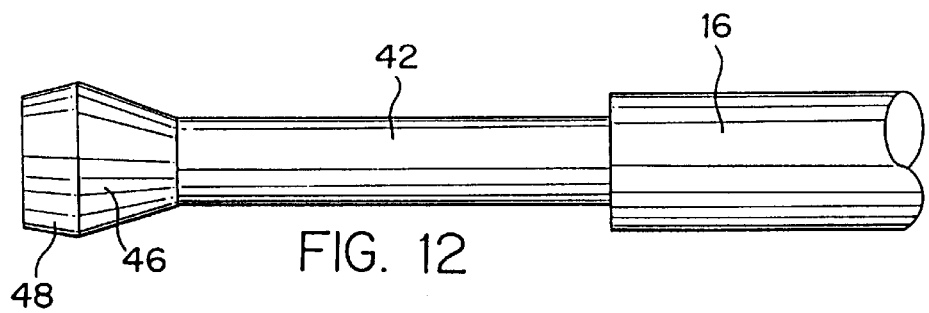
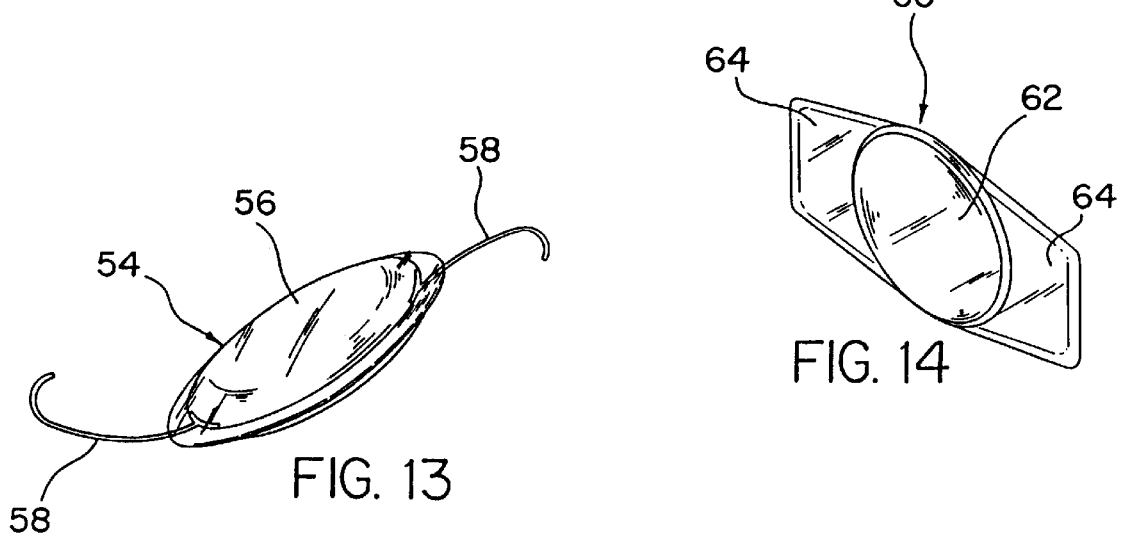
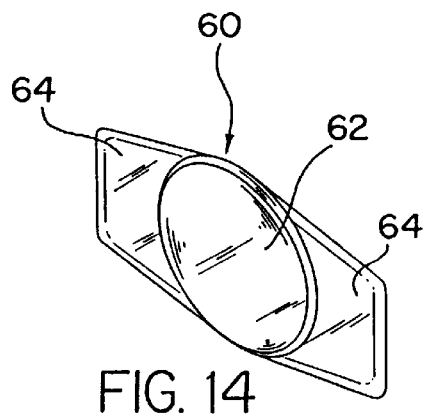
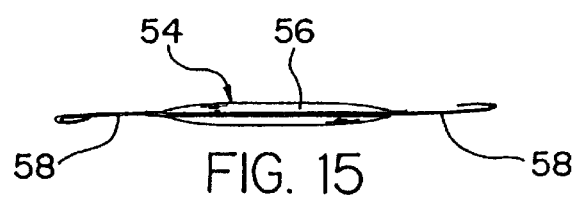

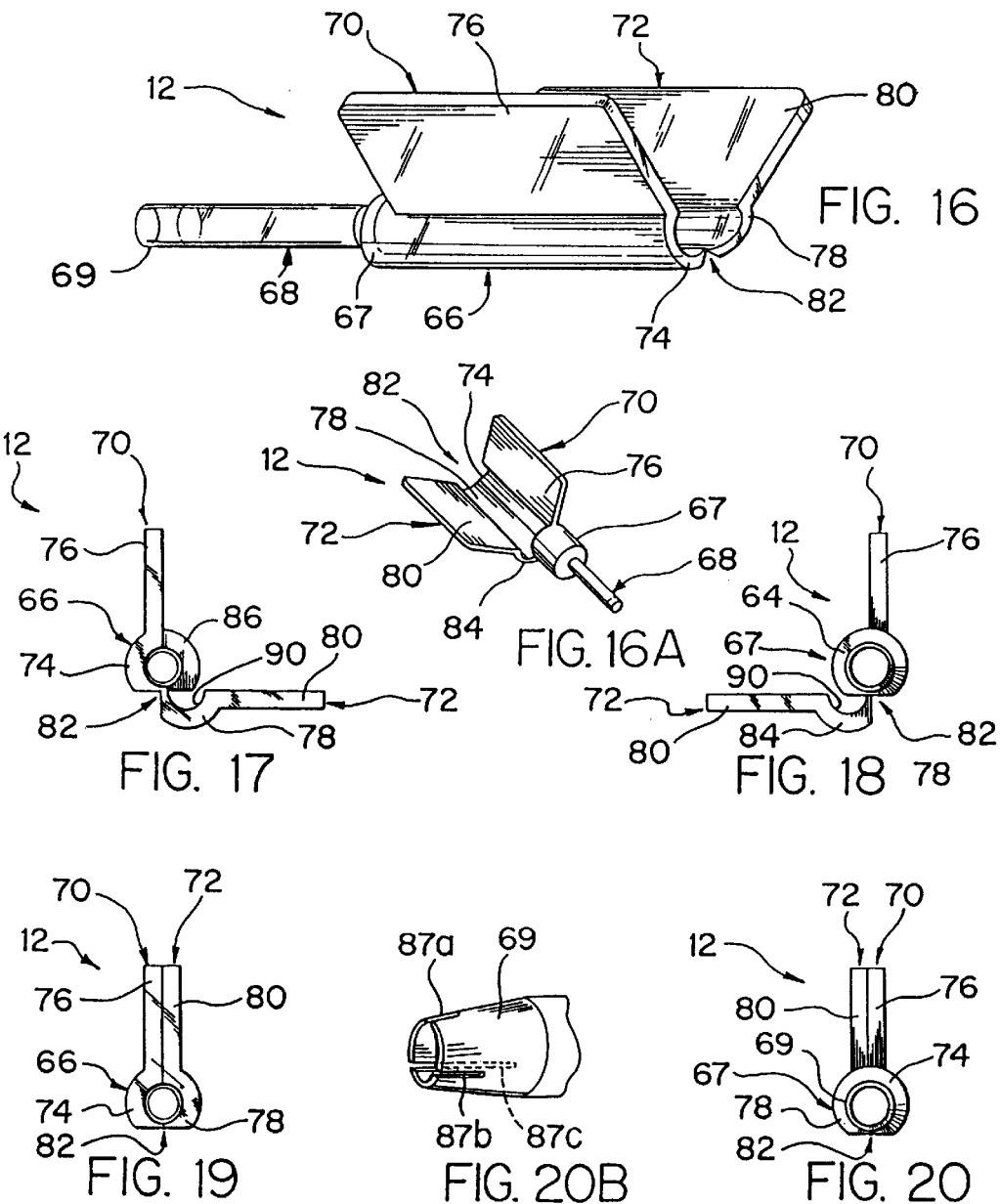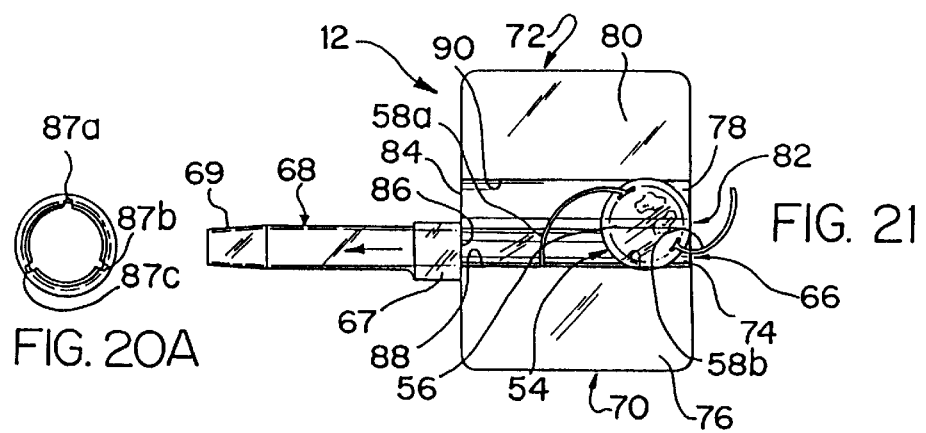

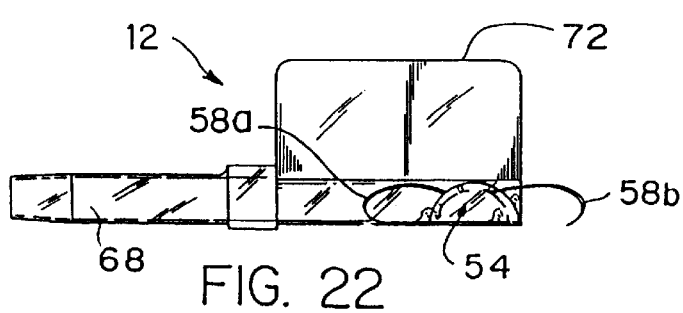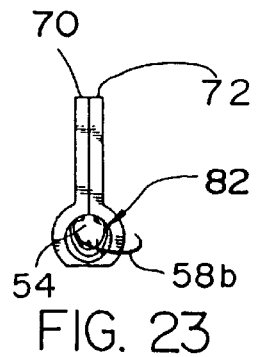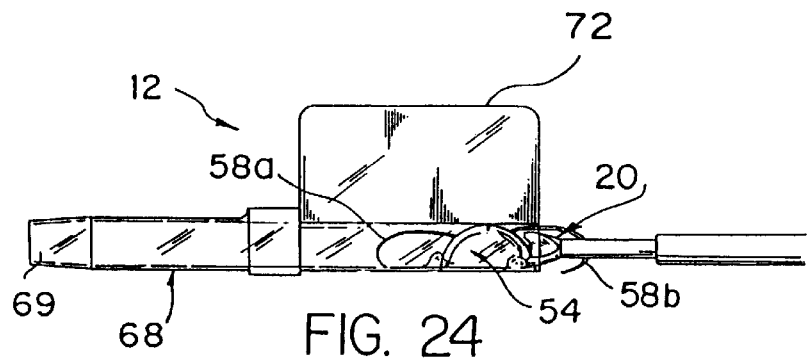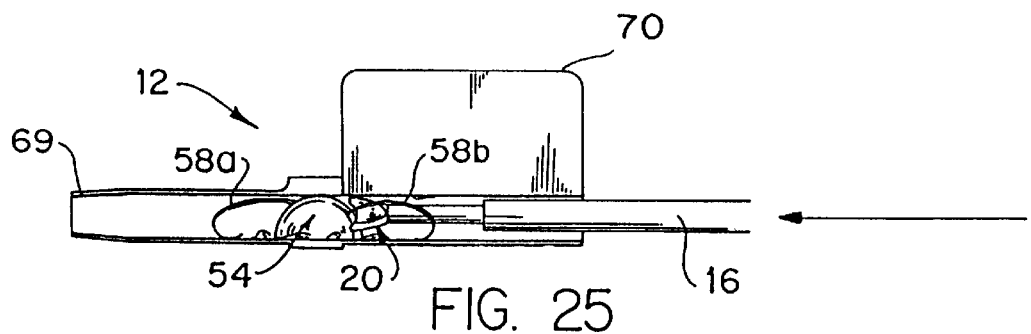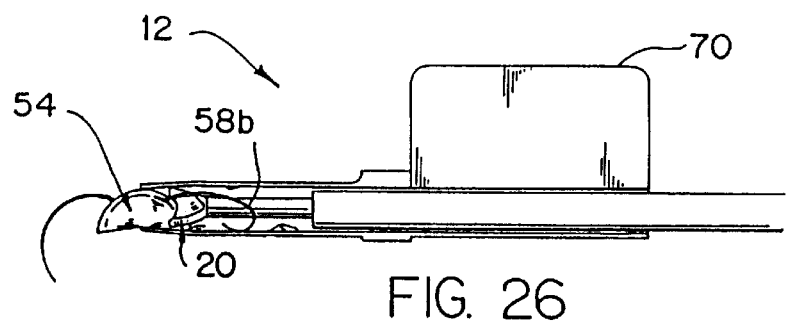

HINGELESS LENS CARTRIDGES FOR INSERTION OF DEFORMABLE INTRAOCULAR LENS

RELATED APPLICATION

This is a continuation-in-part of U.S. patent application Ser. No. 07/953,251, filed on Sep. 30, 1992, now abandoned.

BACKGROUND OF THE INVENTION

1. Field of the Invention

This invention relates to hingeless type intraocular lens microcartridges for use with surgical instruments for implantation of deformable intraocular lenses into the eye.

2. Prior Art

Intraocular lenses have gained wide acceptance in replacement of human crystalline lenses after a variety of cataract removal procedures. The human crystalline lens is generally recognized to be a transparent structure having a thickness of about five (5) millimeters and a diameter of about nine (9) millimeters. The lens is suspended behind the iris by zonula fibers which connect the lens to the ciliary body. A lens capsule surrounds the lens, the front portion of the capsule being commonly known as the anterior capsule and the back portion commonly known as the posterior capsule.

Numerous procedures for the removal of cataracts have been developed in which the lens is removed from the eye and replaced by an artificial lens implant. The extraction procedure may generally be categorized as intracapsular (in which the lens is removed together with the lens capsule) and extracapsular (in which the anterior capsule is removed with the lens, and the posterior capsule is left intact).

Since Ridley implanted the first artificial lens in about 1949, the problems associated with cataract extraction and lens implantation have received a great deal of attention from ophthalmic surgeons. Various types of artificial lenses have been proposed, and appropriate surgical procedures have been developed which strive to reduce patient discomfort and to reduce postoperative complications Reference is made in this connection to Pseudophakos by N. Jaffe et al.; "History of Intraocular Implants" by D. P. Choyce (Annals of Ophthalmology, October 1973); U.S. Pat. Nos. 4,251,887 issued to Anis on Feb. 24, 1981; 4,092,743 issued to Kelman on Nov. 8, 1977; "Comparison of Flexible Posterior Chamber Implants", presented at the American Intraocular Implant Society Symposium Apr. 23, 1982, by Charles Berkert, M.D.; and "the Simcoe Posterior Lens" (Cilco, Inc. 1980); U.S. Pat. No. 4,573,998 issued to Mazzocco on Mar. 4, 1986, and U.S. patent application Ser. No. 400,665 for "Improved Fixation System for Intraocular Lens Structures", filed Jul. 22, 1982, U.S. Pat. Nos. 4,702,244 issued to Mazzocco on Oct. 27, 1987; and 4,715,373 issued to Mazzocco et al. on Dec. 29, 1987, which disclosures are hereby incorporated by reference.

Of particular interest in the context of the present invention is the development of surgical techniques requiring relatively small incisions in the ocular tissue for the removal of cataracts as disclosed in U.S. Pat. Nos. 4,002,169 and 3,996,935. A number of skilled artisans have disclosed intraocular lens structures comprising an optical zone portion generally made of rigid materials such as glass or plastics suitable for optical use.

However, one of the principal disadvantages of the conventional rigid intraocular lens is that implantation of the lens requires large incisions in the ocular tissue. This type of surgical procedure leads to a relatively high complication rate, among other disadvantages. For instance, the serious dangers associated with implantation of a rigid lens structure include increased risk of infection, retinal detachment, and laceration of the ocular tissue, particularly with respect to the pupil.

Accordingly, those skilled in the art have recognized a significant need for surgical tools for implantation of deformable intraocular lens structures which afford the clinical advantages of using relatively small incision techniques, which provide a safer and more convenient surgical procedure. In particular, those skilled in the art of deformable intraocular lenses and methods and devices for implantation, have also recognized a significant need for surgical tools which do not require widening of the wound made in the ocular tissue during or after implantation, but will deform the intraocular lens to a predetermined cross section in a stressed state and which allow the ophthalmic surgeon to inspect the lens prior to implantation without manipulation in the eye. The present invention fulfills these needs.

The present invention was derived by improving the methods and devices in the above-identified patents, specifically the methods of U.S. Pat. Nos. 4,573,998 and the devices of U.S. Pat. No. 4,702,244.

SUMMARY OF THE INVENTION

An object of the present invention is to provide an improved intraocular lens microcartridge.

Another object of the present invention is to provide a intraocular lens microcartridge for use with a surgical device for implantation of a deformable intraocular lens into the eye through a relatively small incision made in the ocular tissue, said lens microcartridge comprising a lens holder portion having a lens receiving portion for receiving and holding the deformable intraocular lens, and a nozzle portion connected to and extending from said lens holder portion, said lens holder portion and said nozzle portion having a continuous passageway extending therethrough.

A further object of the present invention is to provide an intraocular lens microcartridge with a hingeless construction.

An even further object of the present invention is to provide an intraocular lens microcartridge having a lens receiving portion that is fixed relative to a nozzle portion thereof.

Another further object of the present invention is to provide an intraocular lens microcartridge with a lens receiving portion having an oval shaped barrel configuration.

Another object of the present invention is to provide an intraocular lens microcartridge having a lens receiving portion provided with a longitudinal slot therethrough to allow a deformable intraocular lens to be loaded through the slot.

A further object of the present invention is to provide an intraocular lens microcartridge having a lens receiving portion provided with a longitudinal slot therethrough and extending to an end of a lens holder portion to allow a deformable intraocular lens to be loaded through the slot.

An even further object of the present invention is to provide an intraocular lens microcartridge having a lens receiving portion provided with a longitudinal slot therethrough and extending from a rounded end to an end of a lens holder portion to allow a deformable intraocular lens to be loaded through the slot.

Another further object of the present invention is to provide an intraocular lens microcartridge with a lens holder portion including a transition portion with an oval shaped barrel located between a lens receiving portion and a nozzle portion.

Another object of the present invention is to provide an intraocular lens microcartridge with a lens holder portion including a transition portion with an oval shaped barrel defined by inwardly tapering side walls that taper from the dimensions of the lens receiving portion to the dimensions of the nozzle portion located between a lens receiving portion and a nozzle portion.

A further object of the present invention is to provide an intraocular lens microcartridge with a lens receiving portion provided with an oval shaped barrel a transition portion provided with an oval shape barrel with inwardly tapering sides, and a nozzle portion provided with an inwardly tapering conical passageway defining a continuous passageway through the microcartridge.

An even further object of the present invention is to provide an intraocular lens microcartridge with an oval shaped barrel of a transition portion defined by conical shaped inner side walls, a substantially flat bottom wall, and a top wall having a downwardly extending protrusions that tapers so as to become less pronounced when extending from a lens receiving portion to a nozzle portion.

Another further object of the present invention is to provide an intraocular lens microcartridge with an oval shaped barrel of a transition portion defined by conical shaped inner side walls, a substantially flat bottom wall, and a top wall having a downwardly extending protrusion that tapers so as to become less pronounced when extending from a lens receiving portion to a nozzle portion wherein the inner top wall is substantially parallel to the inner bottom wall.

Another object of the present invention is to provide an intraocular lens microcartridge having an oval shaped barrel in a receiving portion having greater cross-sectional dimensions relative to cross-sectional dimensions of an entranceway into a nozzle portion thereof.

A further object of the present invention is to provide a intraocular lens microcartridge for use with a surgical device for implantation of a deformable intraocular lens into the eye through a relatively small incision made in the ocular tissue, the lens microcartridge comprising a lens holder portion having a lens receiving portion for receiving and holding the deformable intraocular lens, and a nozzle portion connected to and extending from said lens holder portion and having a tapering configuration, the lens holder portion and the nozzle portion having a continuous passageway extending therethrough.

An even further object of the present invention is to provide an intraocular lens microcartridge having an outer wall of a nozzle portion tapering downwardly from a lens holder portion to a free end of the nozzle portion.

Another further object of the present invention is to provide an intraocular lens microcartridge having an inner wall and an outer wall of a nozzle portion tapering together is a direction towards a free end of the nozzle portion providing a wall thickness that tapers thinner from the lens holder portion to the free end of the nozzle portion.

Another object of the present invention is to provide an intraocular lens microcartridge having an extension of the lens microcartridge for aligning the lens microcartridge in a surgical device for implantation of the deformable intraocular lens.

A further object of the present invention is to provide an intraocular lens microcartridge having an extension of the lens microcartridge for aligning the lens microcartridge in a surgical device for implantation of the deformable intraocular lens wherein the extension protrudes upwardly from the lens holder portion.

An even further object of the present invention is to provide an intraocular lens microcartridge for use with a surgical device for implantation of a deformable intraocular lens into the eye through a relatively small incision made in the ocular tissue, the lens microcartridge comprising a lens holder portion having a lens receiving portion defined by a cylinder having a longitudinal slot therethrough for receiving and holding the deformable intraocular lens, the lens holder having a transition portion defined by a tapering inwardly interior wall extending from said lens receiving portion, a nozzle portion connected to and extending from the transition portion of the lens holder portion, the lens holder portion and the nozzle portion having a continuous passageway extending therethrough, and an extension of the lens holder portion for aligning the lens microcartridge in the device for implantation of the deformable intraocular lens.

The present invention is directed to methods and devices for implantation of intraocular lenses into the eye. In particular, the present invention is directed to hingeless type intraocular lens microcartridges.

A surgical device according to the present invention includes the combination of a lens holder and a holder for the lens holder or lens microcartridge. The preferred lens microcartridge comprises the combination of a lens receiver and an implantation nozzle. The lens receiver in one preferred embodiment is defined by a split tubular member having a fixed tubular portion with an extension connected to a moveable tubular portion with an extension at a hinge. This configuration allows the microcartridge to be opened to accept a deformable intraocular lens, and closed to condense the lens into the passageway. The split tubular portion is connected to a nozzle with a continuous passageway passing through the tubular member and the nozzle.

Another preferred embodiment is a hingeless type microcartridge into which a lens is carefully loaded prior to being placed in the receiver of the surgical implantation device.

The lens holder is inserted into a holder (i.e. surgical implantation device) having means for driving or manipulating the lens from the lens holder into the eye. In the preferred embodiment, the holder is provided with a plunger for driving the lens from the lens holder into the eye. Further, the holder is configured to receive the microcartridge having a nozzle of the hinged or hingeless version.

The preferred holder includes means to prevent the microcartridge from rotating within the holder, and means for preventing the plunger from rotating within the holder. The means for preventing rotation of the microcartridge within the holder can be define by providing the microcartridge with one or more extensions that cooperate with the opening of the receiver of the holder to prevent rotation. The means for preventing the plunger from rotating within the holder can be defined by providing the plunger and a sleeve within the holder with a particular cross-sectional shape that prevents rotation, for example, a half-circle shape.

The preferred holder includes a plunger with a threaded cap cooperating with a threaded sleeve of the holder body for dialing the plunger forward within the holder for precise and accurate movement of the lens during the implantation process. The holder is configured so that the plunger can be moved a predetermined distance by sliding motion within the holder body followed by engagement of the threaded cap of the plunger with the threaded sleeve of the holder body to continue the forward progress of the plunger tip.

The preferred plunger tip is defined by a faceted tip having various surfaces for moving and manipulating the lens from the lens holder and within the eye. The tip is designed to provide a clearance between the tip and the inner surface of the passageway through lens holder to accommodate the trailing haptic and prevent damage thereto. Once the lens is inserted into the eye, the tip can be used to push and rotated the lens into proper position within the eye.

A method according to the present invention includes lubricating the surface of a deformable intraocular lens with a surgically compatible lubricant, and loading the lens into a microcartridge in the opened position. The microcartridge is closed while condensing the lens by a folding action into a shape so that it can be forced through the passageway in the microcartridge. The microcartridge is inserted into the holder with the plunger retracted.

The plunger is moved forward in a sliding manner by pushing the plunger forward while holding the holder body still. This action forces the lens from the tubular member portion of the microcartridge into the nozzle portion. At this point the threads of the threaded end cap of the plunger engage with the threads of the threaded sleeve. The threaded end cap is rotate slightly to engage the threads. The device is now ready for the implantation process.

The nozzle of the microcartridge is placed through a small incision in the eye. The threaded end cap of the plunger is rotated or dialed to further advance the lens forward through the nozzle and into the eye. The threaded end cap is further dialed to exposed the tip of the plunger within the eye and push the lens into position. The tip can be used to also rotate the lens within the eye for positioning of the haptics.

BRIEF DESCRIPTION OF THE DRAWINGS

FIG. 1 is a perspective view of one embodiment of device according to the present invention with a lens holding microcartridge positioned in the device for implantation of deformable lens structures for placement in the eye;

FIG. 2 is a perspective view of the surgical device depicted in FIG. 1 with the plunger retracted, and with the lens holding microcartridge removed;

FIG. 3 is a side view of the device depicted in FIG. 2, with the plunger in the extended position;

FIG. 4 is a side elevational view of the device shown in FIG. 1;

FIG. 5 is a detailed longitudinal cross-sectional view of the device shown in FIG. 4;

FIG. 11 is an enlarged detailed right side elevational view of the tip of the plunger in the spacial orientation, as shown in FIG. 4;

FIG. 12 is an enlarged detailed bottom view of the tip of the plunger in the spacial orientation, as shown in FIG. 1;

FIG. 13 is a perspective view of a lens for use in the present invention;

FIG. 14 is a perspective view of another type of lens for use in the present invention;

FIG. 15 is a side view of the lens shown in FIG. 13;

FIG. 16 is a perspective view of the lens holding microcartridge in the open position to allow a lens to be loaded therein;

FIG. 16A is another perspective view of the lens holding microcartridge in the open position;

FIG. 17 is a rear end elevational view of the lens holding microcartridge in the open position;

FIG. 18 is a front end elevational view of the lens holding microcartridge in the open position;

FIG. 19 is a rear end elevational view of the lens holding microcartridge in the closed position;

FIG. 20 is a front end elevational view of the lens holding microcartridge in the closed position;

FIG. 20A is a detailed end view of the nozzle showing three (3) slots of different length equally spaced about the circumference of the tip;

FIG. 20B is a detailed perspective view of the tip showing the three (3) slots of different length;

FIG. 21 is a top planar view of the lens holding microcartridge in the open position;

FIG. 22 is a side elevational view of the lens holding microcartridge in the closed position;

FIG. 23 is a rear end elevational view of the lens holding microcartridge in the closed position;

FIG. 24 is a broken away side view of the device showing the lens holding microcartridge in relationship to the plunger in the retracted position;

FIG. 25 is a broken away side view of the device showing the lens holding microcartridge in relationship to the plunger in a partially extended position;

FIG. 26 is a broken away side view of the device showing the lens holding microcartridge in relationship to the plunger in a fully extended position;

DETAILED DESCRIPTION OF PREFERRED EMBODIMENTS

Figure 6:
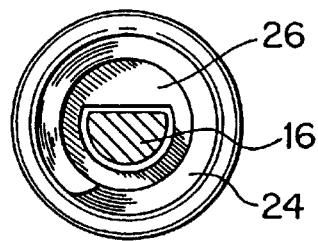
FIG. 6 is a detailed transverse cross-sectional view of the device, as indicated in FIG. 5.
Figure 7:
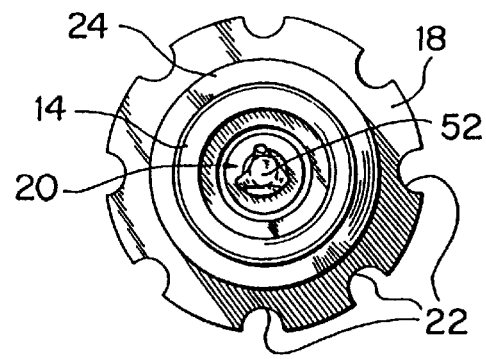
FIG. 7 is a detailed end view of the device, as indicated in FIG. 5.

The present invention is directed to a system including methods and devices for implantation of deformable intraocular lens structures for surgical placement in the eye.

An inventive device according to the present invention comprises a holder having a receiver, a lens holder that can be removably inserted into the receiver of the holder, and means such as a moveable plunger disposed within the holder to force and manipulate the lens from the lens holder into the eye.

Preferably, the lens holder is defined by a lens holding microcartridge for receiving the lens structure. Further, the microcartridge is preferably a structure configured to be opened and closed. The preferred embodiment of the microcartridge receives a lens having prescribed memory characteristics when in the open position, and performs the function of folding or deforming the lens structure into a condensed configuration when being closed. Alternatively, the microcartridge can be a structure having a passageway defined by a continuous walled annulus, and a lens could be inserted into the passageway from the end of microcartridge by compressing, rolling folding, or combination of these techniques prior to insertion into the microcartridge.

Once a lens is positioned into the microcartridge, the microcartridge is positioned into a plunger device. The assembled device maintains the lens in its condensed configuration during insertion into the eye yet permits the deformed lens to return to its original configuration, size and fixed focal length once implanted in the eye, thereby providing a safe, convenient, and comfortable surgical procedure.

A preferred embodiment of a deformable intraocular lens implantation device 10 according to the present invention is shown in FIGS. 1, 2 and 3. The implantation device comprises a microcartridge 12 disposed within a holder 13 comprising a holder body 14 with a receiver 15, and a moveable plunger 16. In FIG. 1, the receiver 15 is defined by an opening 17 through the wall of the holder body 14 of the size and shape shown in FIGS. 1 and 2. The opening 17 is defined by parallel edges 17a, 17a, which are sufficiently spaced apart to allow the microcartridge 12 to be loaded into the receiver 15 of the holder 13, tapered edges 17b, clamping edges 17c, and stop edge 17d. In FIG. 1, the microcartridge 12 is positioned in the receiver 15 between the clamping edges 17c with the plunger extending through the microcartridge 12 in a position, for example, after a lens implantation procedure.

In FIG. 2, the lens holding microcartridge 12 is shown removed from the holder 13 with the plunger 16 in a retracted position for allowing the microcartridge 12 containing a loaded lens and its haptic to be inserted within the holder 13. In FIG. 3, the holder 13 is shown with the plunger 16 in the extended position without the microcartridge 12 for purposes of illustration of the components.

The plunger 16 is fitted with a threaded end cap 18 at one end, and fitted with a tip 20 at an opposite end. The threaded and cap 18 is provided with a plurality of grooves 22 to a allow a person to tightly grip the cap 18 with his or her finger tips. The threaded and cap 18 is received within a threaded sleeve 24 of the insert holder 14. The threaded end cap 18 can be a separate component attached to the insert holder 13, or integral therewith, as shown in the construction is FIG. 5.

The plunger 16 is installed within the holder 13 in a manner to allow the plunger to be reciprocated therein. In the illustrated embodiment, the plunger 16 is supported for sliding movement within the holder 13 by guide 26, as shown in FIGS. 5 and 6. The outer dimension of the guide 26 is approximately the same size as the inner dimensions of the holder 13 to allow the guide to be inserted within the insert holder. During construction, the guide 26 is inserted within the holder 13, and locked into position by pin 28 inserted into a predrilled hole in both the wall of the holder 13 and guide 26.

The cross-sectional shape of the plunger 16 as well as the shape of the inner surface of the guide 26 are approximately a half-circle, as shown in FIG. 6. This arrangement prevents the plunger 16 from rotating within the holder 13 to maintain the orientation of the tip 20 relative to the holder 13 during operation.

The threaded end cap 18 is connected to the plunger 16 in a manner to allow the threaded end cap 18 to be rotated relative to the plunger 16. For example, the left end of the plunger 16 (FIG. 5) is provided with a threaded extension 30, which is secured to the threaded end cap 18 by a nut 32. Specifically, the threaded end cap 18 is manufactured with external threads 34 and a longitudinal center bore 36 that ends on the right side of the threaded end cap 18 leaving a wall 38.

The wall 38 is provided with a hole slightly larger than the outer diameter of the threaded extension 34 to allow the threaded end cap 18 to freely rotate on the plunger 16 while being secured to the end of the plunger 16. During construction, the nut 32 is inserted through the center bore 36 and threaded onto the extension 30 to secure the threaded end cap 18 to the plunger 16. A curved cap 40 is press fitted into the end of the center bore 36 to seal the center bore 36 to prevent debris from entering therein during use.

Figure 8:
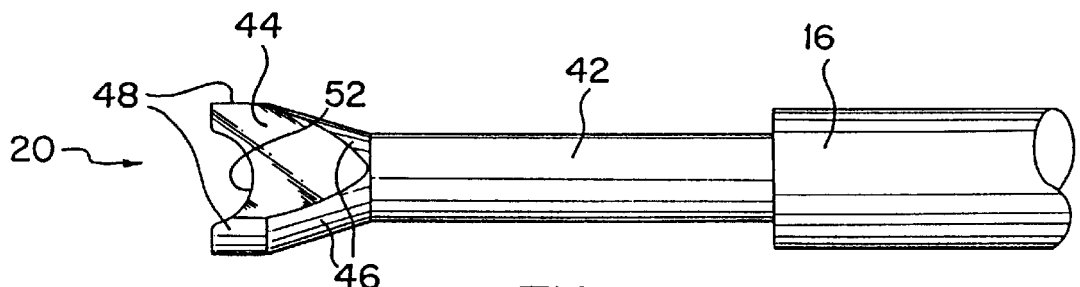
FIG. 8 is an enlarged detailed left side elevational view of the tip of the plunger in the spacial orientation as shown in FIG. 1.
Figure 9:
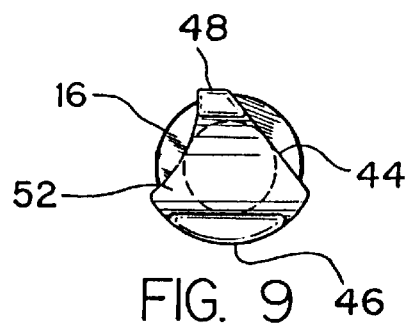
FIG. 9 is an enlarged detailed end view of the tip shown in FIG. 8.
Figure 10:
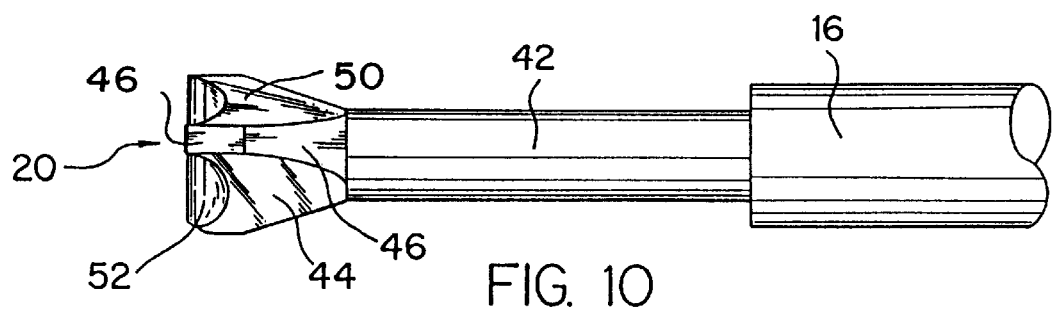
FIG. 10 is an enlarged detailed top planar view of the tip of the plunger.
Figure 27:
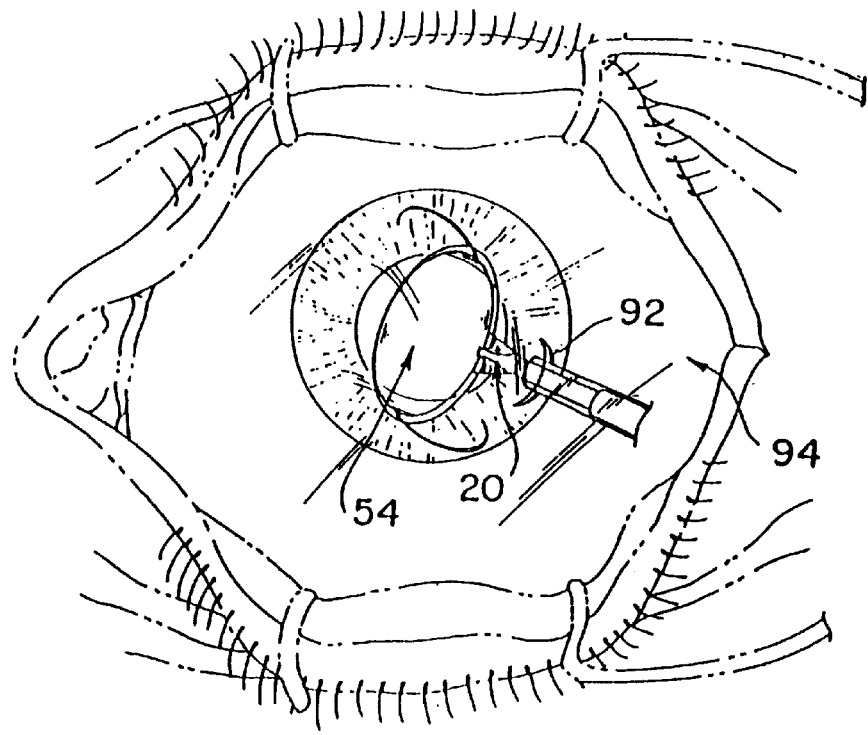
FIG. 27 is a perspective view showing the device positioning a deformable intraocular lens within the eye.

The details of the tip arrangement are shown in FIGS. 7 to 12. The plunger 16 is manufactured with an extension 42 supporting tip 20. The tip 20 structure provides means for inserting the deformable intraocular lens into the eye and manipulating the lens within the eye after the insertion step. For example, the tip 20 is faceted in the manner shown in the figures. Specifically, the left side of the tip 20 shown in FIG. 8 is provided with a flat surface facet 42, conical surface 44, and cylindrical surface 46. The right side shown in FIG. 11 is provided with a concave surface facet 50.

The end face of the tip 20 is designed to push the lens into position once inserted into the eye. For example, the end face is defined by a concave cylindrical surface 52 shown in FIG. 8.

Suitable deformable intraocular lens for use in the present invention are shown in FIGS. 13–15. The deformable intraocular lens 54 shown in FIGS. 13 and 15 includes a lens body 56 with attachment means defined by a pair of haptics 58 each having one end anchored in the lens portion 56 and a free end for attachment to the eye tissue. The deformable intraocular lens 60 shown in FIG. 14 includes a lens body 62 and attachment means defined by a pair of lateral lobes 64 of the lens portion 62.

The details of the preferred lens holding microcartridge 12 are shown in FIGS. 16–20. The microcartridge 12 comprises a split tubular member 66 extending to a continuous tubular member 67 and an implantation nozzle 68. When the microcartridge is in a closed position, a continuous circular or oval passageway of the same diameter extends through the split tubular member 66 through the continuous tubular member 67 and through the implantation nozzle 68. The microcartridge is preferably made of injection molded plastic such as polypropylene. The split tubular member 66 is defined by a fixed portion 70 and a moveable portion 72. The fixed portion 70 is fixed relative to the implantation nozzle 68, and is defined by a tubular portion 74 and extension 72. The moveable portion 72 is moveable relative to the fixed portion 70 for opening and closing the split tubular member 66. The moveable portion 72 is defined by a tubular portion 78 and extension 80. A hinge 82 is provided between the fixed portion 70 and moveable portion 72. The hinge 82 is defined by reducing the thickness of the walls of the tubular portion 74 and 75 at the hinge 82, as shown in FIGS. 17, 18 and 19. The hinge 82 runs the length of the split tubular member 66 to allow the extension 76 and 78 to be split apart, or brought together to open and close, respectively, the split tubular member 66.

The tubular portion 78 of the moveable portion 72 is provided with a sealing edge 84, which is exposed when the lens holding microcartridge 12 is opened, as shown in FIG. 16A, and seals with a similar sealing edge 86 (See FIGS. 17 and 21) of the continuous tubular member 67 when the lens holding microcartridge is closed.

The end of the tip 20 is provided with three (3) equally spaced slots 87a, 87b and 87c of different length provided about the circumference thereof, as shown in FIGS. 20A and 20B. The slot 87a positioned at the top of the tip 20 is the shortest, slot 87c on the right side of the tip 20 is the longest, and slot 87b on the left side is of medium length. The slots 87a, 87b, 87c cause the lens 54 to rotate as it exits the tip 20.

Other embodiments of the microcartridge 12 according to the present invention are shown in FIGS. 30–33.

Figure 30:
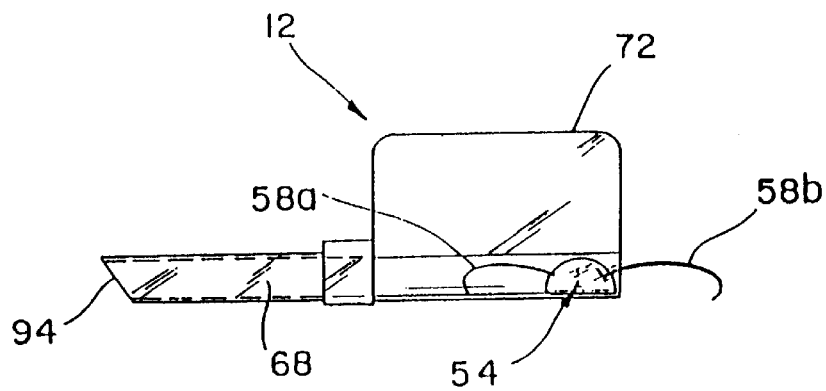
FIG. 30 is a side elevational view of an alternative embodiment of the lens holding microcartridge provided with a beveled tip.

The microcartridge shown in FIG. 30 is provided with a beveled tip 94 to facilitate entry of the tip through the incision in the eye during implantation. The beveled tip 94 can be set at approximately forty-five (45) degrees relative to the passageway through the microcartridge 12.

Figure 31:
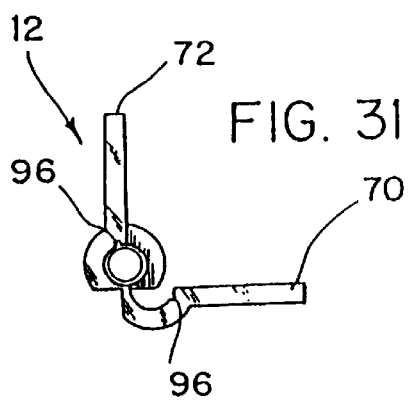
FIG. 31 is a rear end elevational view of another alternative embodiment of the lens holding microcartridge provided with grooves in the passageway to facilitate folding the cartridge in an open position.
Figure 32:
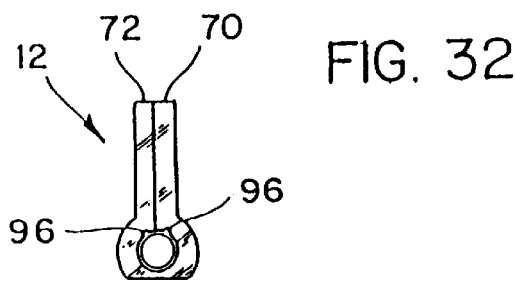
FIG. 32 is a rear end elevational view of another alternative embodiment of the lens holding microcartridge provided with grooves in the passageway to facilitate folding the cartridge in a closed position.

The embodiment of the microcartridge shown in FIGS. 31 and 32 is provided with a set of grooves 96 provided inside the passageway therethrough. The grooves accommodate the edges of the lens being loaded into the microcartridge to facilitate bending of the lens. Specifically, the edges of the lens are placed in the grooves 96 to prevent relative slippage of the edges with the inner surface of the passageway through the microcartridge when the microcartridge is being folded into the closed position.

Figures 33A, 33B:
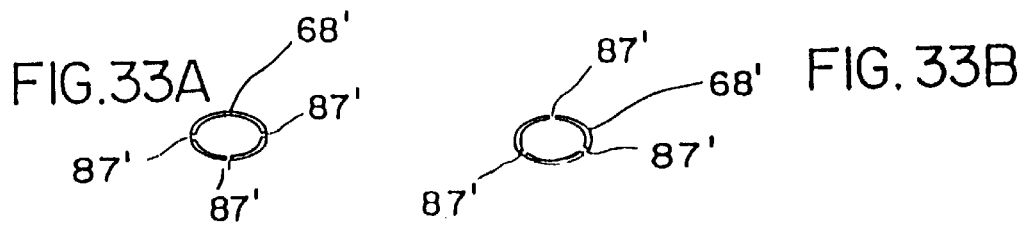
FIG. 33A is a front end elevational view of the nozzle of an alternative embodiment of the lens holding microcartridge.
FIG. 33B is a front end elevational view of the nozzle of a further alternative embodiment of the lens holding microcartridge.

The embodiments of the microcartridge shown in FIGS. 33A and 33B each have a nozzle 68, having an oval cross-section with slots 87' differently position as shown, respectively, again to facilitate entry through an incision in the eye. Alternatively, the cross-section can be two half circles set apart and connected together rather than oval.

The various features of the microcartridges shown in FIGS. 16–21 and 30–33 can be used in various combinations to achieved an optimum design for a particular application. However, all of these features are typically considered improvements of the basic combination.

The components of the device 10, except for the microcartridge 12, are preferably fabricated from autoclavable material such as stainless steel or from a disposable rigid plastic such as medical grade ABS or the like.

Hingeless Intraocular Lens Microcartridge

A preferred embodiment of the hingeless type intraocular lens microcartridge according to the present invention are shown in FIGS. 34–43.

Figure 35:
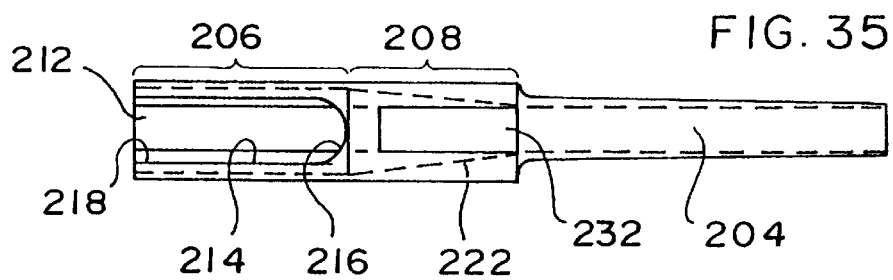
FIG. 35 is a top view of the hingeless intraocular lens microcartridge, as shown in FIG. 34.
Figure 36:
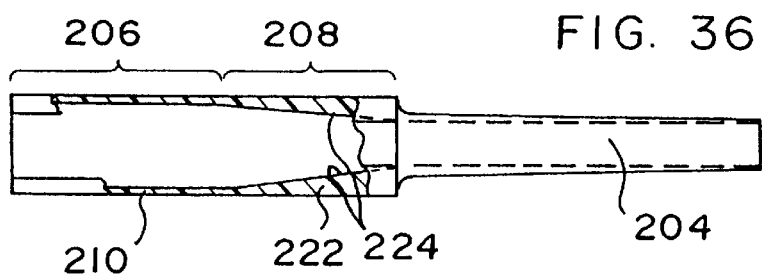
FIG. 36 is a partial broken away top view of the hingeless intraocular lens microcartridge, as shown in FIG. 35.

In this embodiment, the lens microcartridge 200 comprises a lens holder portion 202 and a nozzle portion 204 connected to and extending from one end of the lens holder portion 202. The lens microcartridge is provided with a continuous passageway therethrough that extends from one end of the lens microcartridge to the other end thereof. The lens holder portion 202 includes a receiver portion 206 for receiving a deformable intraocular lens and a transition portion 208, as shown in FIGS. 35 and 36.

The receiver portion 206 is defined by a tubular member 210 provided with an oval shaped barrel 212 having a longitudinal slot 214 therethrough. The oval shaped barrel 212 has a constant cross section or a gradually reducing cross section throughout the length of the receiver portion 206. Further, the longitudinal slot 214 has a rounded end 216 at one end, and an open end 218 at an opposite end thereof.

Figure 34:
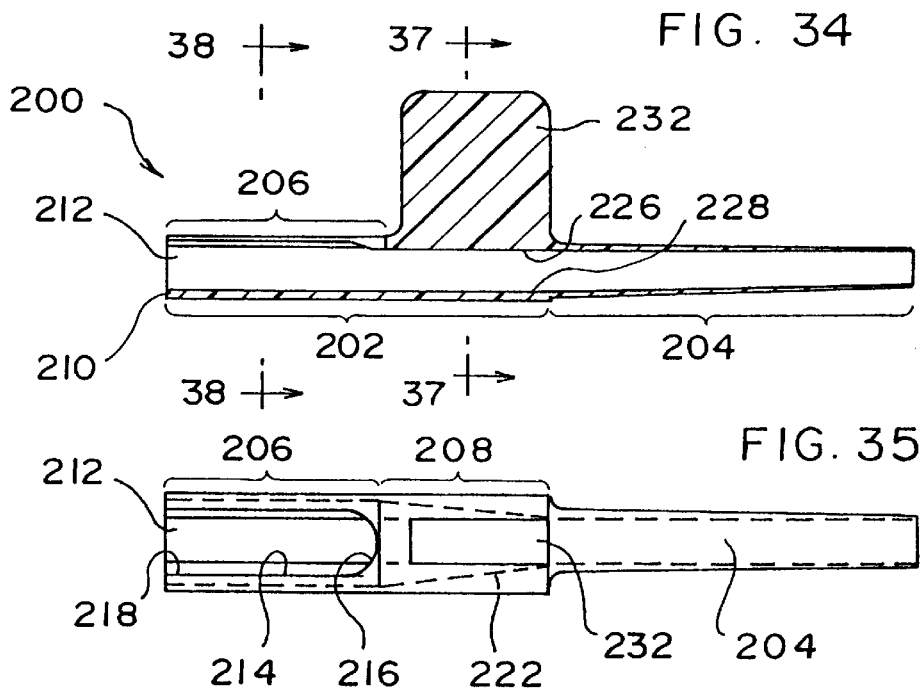
FIG. 34 is a longitudinal cross-sectional view of a preferred embodiment of the hingeless intraocular lens microcartridge according to the present invention.
Figure 37:
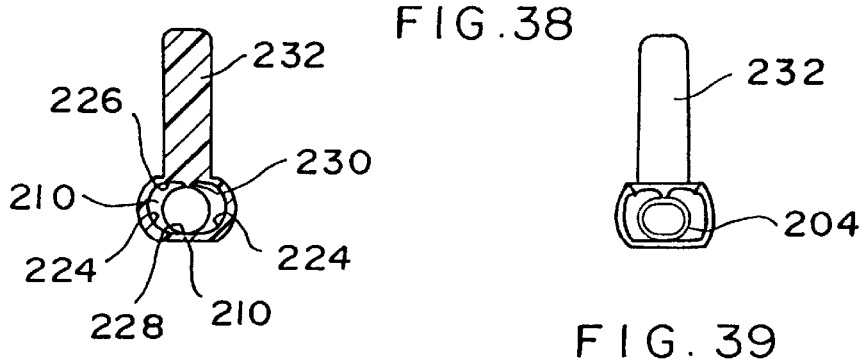
FIG. 37 is a cross-sectional view of the hingeless intraocular lens microcartridge at location 37—37, as shown in FIG. 34.
Figure 39:
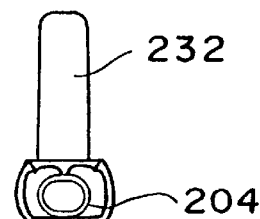
FIG. 39 is a front elevational view of the hingeless intraocular lens microcartridge shown in FIGS. 34–37.
Figure 40:
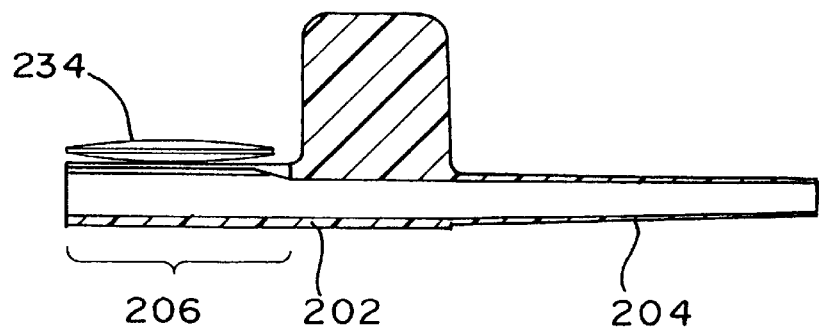
FIG. 40 is a longitudinal cross-sectional view of the hingeless intraocular lens microcartridge, as shown in FIG. 34, with an intraocular lens placed on top of the microcartridge ready for insertion therein.
Figures 41, 42, 43:
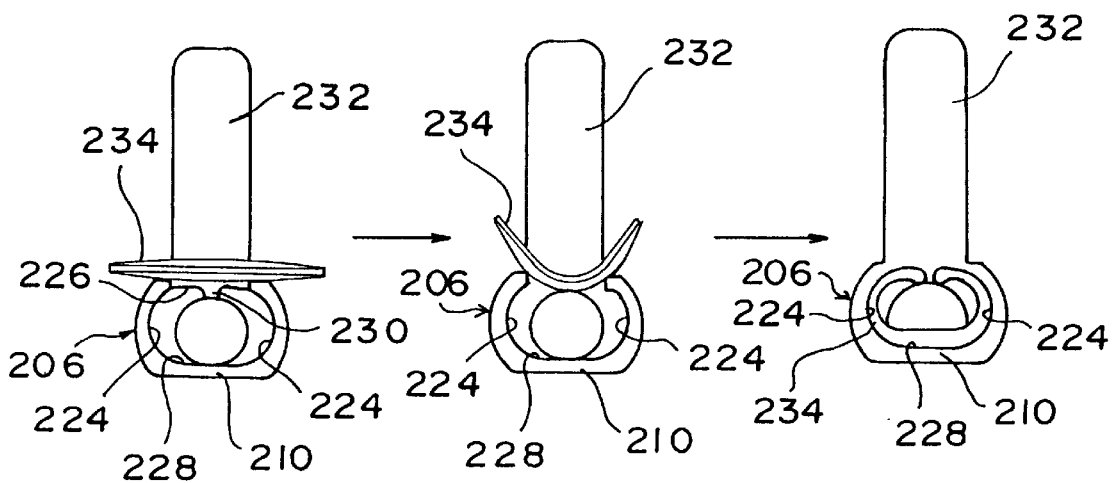
FIG. 41 is a rear elevational view of the microcartridge, as shown in FIG. 40, with the intraocular lens not yet deformed for inserting into the microcartridge.
FIG. 42 is a rear elevational view of the microcartridge, as shown in FIG. 40, with the intraocular lens partial deformed and bent at the center being inserted into the microcartridge.
FIG. 43 is a rear elevational view of the microcartridge, as shown in FIG. 40, with the intraocular lens fully deformed and inserted inside the microcartridge.

The transition portion 208 is defined by a tubular member 220 with an oval shaped barrel 222 having a cross section that tapers inwardly from the receiver portion 206 to the nozzle portion 204. Specifically, the sides 224 of oval shaped barrel 222 taper inwardly, as shown in FIG. 36, while the top surfaces 226 (i.e. defining grooves 226) and bottom surface 228 of the oval shaped barrel 222 are parallel (i.e. not tapered), as shown in FIG. 34. Further, the top 226 is provided with a downwardly extending protrusion 230 having curved sides that are shaped to turn the edges of the deformable intraocular lens downwardly, as shown in FIG. 37. The protrusion becomes less pronounces in a direction extending towards the nozzle portion 204, and disappears at the nozzle portion to a provide a continuous inner surface and transition from the lens holder 202 portion into the nozzle portion 204.

Figure 38:
FIG. 38 is a cross-sectional view of the hingeless intraocular lens microcartridge as indicated at 38—38, as shown in FIG. 34.

The grooves 226 in the receiver portion 206, as shown in FIG. 38, are defined by curled upper portions of the receiver portion 206 on either side of the slot 214, and extend continuously to the grooves of the transition portion 208.

The lens microcartridge 200 is provided with an extension 232 for aligning the lens microcartridge 200 in the device for implantation of the intraocular lens. Specifically, the extension 232 is defined by plastic material that extends from the lens holder portion 202, and is configured to snag fit in the slot of the device for implantation of the intraocular lens. In the embodiment shown in FIGS. 34–39, the extension 232 has a rectangular side profile (See FIG. 34) and has a constant thickness (See FIG. 35) along its length.

The manner in which the deformable intraocular lens is inserted into the lens microcartridge is illustrated in FIGS. 40–43.

A deformable intraocular lens 234 is loaded on top of the receiver portion 206 of the lens holder portion 202. The deformable intraocular lens 234 is forced downwardly in the center thereof by implement or finger tip to reach the configuration shown in FIG. 42. The deformable intraocular lens is further pushed into the receiver portion 206 until it is fully inserted in the oval shaped configuration shown in FIG. 43 with its outer surface wrapping around and in contact with the sides 224, bottom 228, and top 226 of the receiver portion 206. The grooves defined by surfaces 226 hold the lens in position and guide it while the lens is being pushed through the microcartridge by the insertion instrument.

The edges of the deformable intraocular lens 234 contact with the downwardly extending protrusion 230 in the top 226, and ride along the protrusion 230 when being inserted through the lens microcartridge gently further folding the lens as it enters into the nozzle portion 204.

Figure 44:
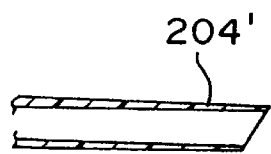
FIG. 44 is a partial view of an alternative tip portion of the microcartridge having a beveled end.
Figure 45:
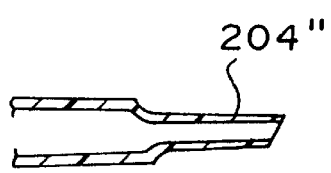
FIG. 45 is a partial view of another alternative tip portion of the microcartridge having a heat deformed tip.

An alternative nozzle portion 204' is shown in FIG. 44 having a beveled end. A further alternative nozzle portion 204" is shown in FIG. 45 having a heat deformed tip with a beveled end. Specifically, the end of the nozzle is heated and stretch to reach the shape and configuration shown.

Methods of Implantation

The surgical procedure begins by coating the lens with a surgically compatible lubricant, and loading the lens into the microcartridge. For example, as shown in FIG. 21, a lens 54 having a lens body 56, a leading haptic 58a is loaded into the microcartridge 12 while a trailing haptic 58b remains trailing outside the microcartridge in the manner shown. Specifically, the lens 54 is loaded downwardly into the opened microcartridge 12 until it sits on the inner surfaces of the tubular portions 74 and 78, for example, with a pair of tweezers. The outer circumferential surface of the lens 54 are held by edges 88 and 90 of the tubular portions 74 and 78, respectively. The rear edge of the lens 54 is placed approximately at the rear edge of the microcartridge 12. The lens 54 is further manipulated to situate the haptics 58a and 58b in the manner shown. Specifically, haptic 54a is positioned in a leading position and the other haptic 54b is positioned in a trailing position outside with respect to the direction of implantation, as indicated by the arrow.

Subsequently, the split tubular member 66 of the microcartridge 12 is closed about the lens 54 by forcing the extensions 76 and 80 together with his or her finger tips. The inner surfaces of the tubular portions 74 and 78 bend and fold the lens 54 when the extensions 76 and 80 are forced together, as shown in FIGS. 22 and 23. Due to the resilient nature of the deformable intraocular lens 54, the lens 54 conform to the curved inner surface of the tubular portions 74 and 78 without damage thereto, as shown in FIG. 23.

The microcartridge 12 containing the loaded lens 54 is inserted between the edges 17a, 17a of the opening 17 into the receiver 15 of the holder 13. As the microcartridge 12 is moved forward, the extensions 76 and 80 move past the tapered edges 17b and come to a stop position between the clamping edges 17c when front portions of the extensions 76 and 80 contact with the stop edge 17d. The clamping edges 17c prevent rotation of the microcartridge inside the holder 13.

The user pushes the threaded end cap 18 forward while securing the holder body 14 from movement, forcing the plunger 16 forward within the holder. As the plunger 16 is moved forward, the tip 20 enters into the rear of the microcartridge 12 and misses the trailing haptic 58B until the tip makes contact with the loaded lens 54, as shown in FIG. 24. As the plunger 16 is moved forward in this manner, the lens 54 previously lubricated is forced into the implantation nozzle 68 of the microcartridge 12, as shown in FIG. 25.

Once the lens 54 enters the implantation nozzle 68, the threads of the end cap 18 contact with the threads of the sleeve 24 stopping further movement of the plunger 14 forward in this manner. The end cap 18 is slightly rotated to engage the threads of the end cap 18 with the threads of the sleeve 24. At this point, the surgical device is ready for the implantation step. The nozzle is insert through the incision in the eye, and the end cap 18 is rotated to continue the forward movement of the plunger 16 by continued rotation of the end cap 18 relative to the holder body 14 to expel the lens from the nozzle into the interior of the eye, as shown in FIG. 26. This manner of screw advancement for moving the plunger 16 forward provides for precise control and accuracy concerning forcing the lens 54 through the remaining portion of the tip 68 into the eye during the implantation procedure. The deformed lens after exiting the nozzle 16 returns to its original configuration, full size and fixed focal length.

Figure 28:
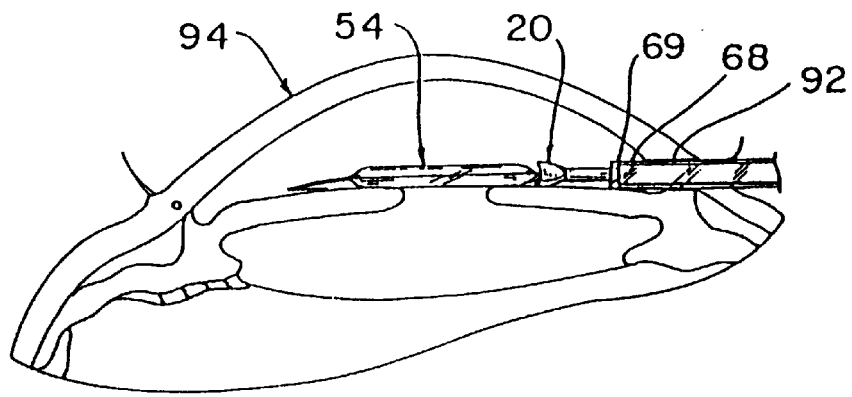
FIG. 28 is a cross-sectional view of an eye showing the positioning of the deformable intraocular lens into position in the eye by the surgical device.
Figure 29:
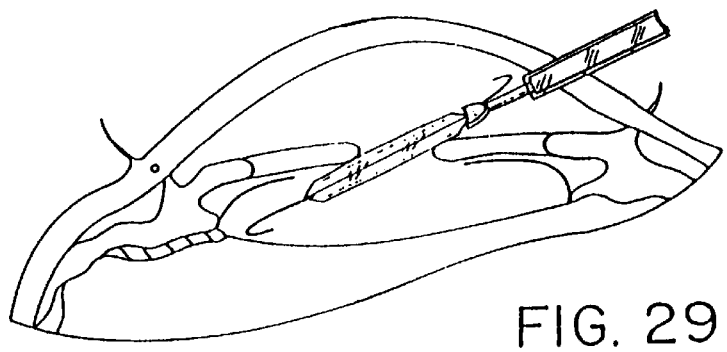
FIG. 29 is a cross-sectional view of an eye showing the positioning of the deformable intraocular lens into a different position in the eye by the surgical device.

After the lens is inserted into the eye, the end cap 18 is further rotated to fully expose the tip 20 of the plunger 16, as shown in FIGS. 28 and 29, to allow the lens to be pushed forward, side manipulated to rotate the lens, and pushed down to properly position the lens within the eye without the aid of other surgical instruments.

The configuration of the tip 20 is important during the implantation process. The faceted tip 20 provides a clearance between the tip 20 and the inner surface of the passageway through the microcartridge 12 to accommodate the trailing haptic 58b during movement of the lens within the microcartridge 12, as shown in FIGS. 25 and 26. Specifically, there exists a sufficient clearance between the flat surface facet 44 and the inner wall of the passageway through the microcartridge 12. During the implantation process, the trailing haptic floats around in the space between the extension 42 of the tip 20 and the inner wall of the passageway, as shown in FIG. 25. This prevents any chance of damage to the trailing haptic, for example, by being caught between the tip 20 and the lens 54 during the implantation process. The leading haptic moves through the passageway unimpeded during the implantation process preventing any damage thereto.

I claim:

1. A lens cartridge for use in a surgical device having a lens cartridge receiver for implantation of a deformable intraocular lens into an eye through a relatively small incision made in the ocular tissue, said lens cartridge comprising:

a hingeless lens holding portion having a lens receiver for receiving and holding the deformable intraocular lens;

a nozzle portion connected to and extending from said lens holding portion, said nozzle portion having a continuous substantially annular wall sad lens holding portion and said nozzle portion having a passageway extending therethrough; and an alignment device defining a portion of the lens cartridge for aligning the lens cartridge in the lens ridge receiver of the surgical device, wherein the lens cartridge is configured to be removably accommodated and positively locked in the lens cartridge receiver of the surgical device, and a tip of said nozzle portion is inserted through relatively small incision in ocular tissue for implantation of the deformable intraocular lens into a eye.

2. A lens cartridge according to claim 1, wherein said lens receiver comprises a lens receiving passageway portion of said passageway extending through the lens cartridge.

3. A lens cartridge according to claim 2, wherein said lens receiver is accessible from one end of the lens cartridge.

4. A lens cartridge according to claim 1, wherein said lens receiver is accessible from a side of the lens cartridge.

5. A lens cartridge according to claim 4, wherein said lens receiver comprises a slot and said deformable intraocular lens is loaded through said slot.

6. A lens cartridge according to claim 5, wherein said slot is a longitudinal slot having one end extending to and opening at one end of the lens cartridge.

7. A lens cartridge according to claim 5, wherein said slot comprises a longitudinal slot having a length the same or greater than a length of the deformable intraocular lens.

8. A lens according to claim 1, wherein said passageway through the lens cartridge comprises an inwardly tapering portion for further folding or compressing the deformable intraocular lens as the deformable intraocular lens moves through said passageway.

9. A lens cartridge according to claim 1, wherein said lens holding portion comprises a transition portion having an inwardly tapering passageway portion connecting a passageway portion extending through said lens receiving portion to a passageway portion extending through said nozzle portion.

10. A lens cartridge according to claim 9, wherein said passageway portion through said side lens receiver is generally oval shaped, said passageway portion through said transition portion is inwardly tapering and generally oval shaped, and said passageway portion through said nozzle portion is inwardly tapering and generally conical shaped defining a continuous passageway through the lens cartridge.

11. A lens according to claim 1, wherein a passageway portion through said lens receiving portion is provided with a pair of longitudinal grooves for guiding the deformable intraocular lens through said passageway.

12. A lens cartridge according to claim 10, wherein said generally oval shaped passageway portion through said transition portion comprises conical shaped inner side walls, a substantially flat bottom wall, and a top wall comprising a pair of inwardly tapering grooves located on opposite side of a protrusion that becomes less pronounced when extending in a direction from said lens receiving portion to said nozzle portion.

13. A lens cartridge according to claim 12, wherein said inner top wall is substantially parallel to said inner bottom wall.

14. A lens cartridge according to claim 5, wherein said longitudinal slot comprises a pair of side edges for supporting side portions of a deformable intraocular lens so that a center portion of the deformable intraocular lens can be forced into said side receiver for folding the deformable intraocular lens when being loaded into said side receiver.

15. A lens cartridge according to claim 1, wherein a passageway portion through said nozzle portion is inwardly tapering.

16. A lens cartridge according to claim 15, wherein an outer surface of said nozzle portion tapers inwardly in a direction from said lens holder portion to a free end of said nozzle portion.

17. A lens cartridge according to claim 15, wherein an inner surface of said nozzle portion tapers inwardly in a direction from said lens holder portion to a free end of said nozzle portion.

18. A lens cartridge according to claim 16, wherein said nozzle portion is provided with a beveled end.

19. A lens cartridge according to claim 18, wherein said inner surface and said outer surface of said nozzle portion taper together in a direction from said lens holding portion to the free end of said nozzle portion providing a wall thickness that tapers thinner in a direction from said lens holding portion to said free end of said nozzle portion.

20. A lens cartridge according to claim 1, wherein said alignment device is associated with said lens holding portion.

21. A lens cartridge according to claim 20, wherein said alignment device comprises an extension protruding outwardly from said lens holding portion.

22. A lens cartridge for use in a surgical device having a lens cartridge receiver for implantation of a deformable intraocular lens into an eye through a relatively small incision made in the ocular tissue, said lens cartridge comprising:

a lens holding portion having a lens receiver comprising a cylinder having a side longitudinal slot through said cylinder for receiving and holding the deformable intraocular lens, said lens holding portion comprising a transition portion with an inwardly tapering passageway portion;

a nozzle portion connected to and extending from said transition portion of said lens holding portion, said lens holding portion and said nozzle portion having a passageway extending therethrough; and an alignment device defining a portion of the lens cartridge for aligning the lens cartridge in the lens cartridge receiver of the surgical device for implantation of the deformable intraocular lens, said alignment device being configured to allow the lens cartridge to be removably connected and positively locked within the lens cartridge receiver of the surgical device.

23. A lens cartridge for use in a surgical device having a lens cartridge receiver for implantation of a deformable intraocular lens into an eye through a relatively small incision made in the ocular tissue, said lens cartridge comprising:

a hingeless lens holding portion;

a nozzle portion connected to and extending from said lens holding portion said nozzle portion having a continuous, substantial annular wall, said lens holding portion and said nozzle portion having a passageway extending therethrough; and a lens receiver provided in a side of the lens cartridge; and an alignment device defining a portion of the lens cartridge for aligning the lens cartridge in the lens cartridge receiver of the surgical device, wherein the lens cartridge is configured to be removably accommodated and positively locked in the lens cartridge receiver of the surgical device, and a tip of said nozzle portion is inserted through a relatively small incision in ocular tissue for implantation of the deformable intraocular lens into an eye.

24. A lens cartridge according to claim 23, wherein said lens receiver is accessible from one end of the lens cartridge.

25. A lens cartridge according to claim 23, wherein said lens receiver comprises a slot in the side of the lens cartridge.

26. A lens cartridge according to claim 25, wherein said slot comprises a longitudinal slot extending along a length of the lens cartridge.

27. A lens cartridge according to claim 26, wherein said slot extends to one end of the lens cartridge.

28. A lens cartridge according to claim 26, wherein said slot extends only a portion of the length of the lens cartridge.

29. A lens cartridge according to claim 27, wherein said slot has a length the same as or greater than the length of the deformable intraocular lens.

30. A lens ridge according to claim 28, wherein said slot is located in said lens holding portion.

31. A lens cartridge according to claim 29, wherein said slot is located in said lens holding portion.

32. A lens cartridge for use in a surgical device having a lens cartridge receiver for implantation of a deformable intraocular lens into an eye through a relatively small incision made in the ocular tissue, said lens cartridge comprising:
 a hingeless lens holding portion;
 a nozzle portion connected to and extending from said lens holding portion, said lens holding portion and said nozzle portion having a passageway extending therethrough, said passageway having at least one groove extending along at least a portion of the length of said passageway; and
 an alignment device defining a portion of the lens cartridge for aligning the lens cartridge in the lens cartridge receiver of the surgical device,
 wherein the lens cartridge receiver is configured to be removably accommodated and positively locked in the lens cartridge receiver of the surgical device, and a tip of said nozzle portion is inserted through a relatively small incision in ocular tissue for implantation of the deformable intraocular lens into an eye.

33. A lens cartridge according to claim 32, wherein said at least one groove is located in a portion of said passageway extending through said lens holding portion of the lens cartridge.

34. A lens cartridge according to claim 33, wherein said portion of said passageway having said at least one groove transitions to a grooveless portion of said passageway extending through said nozzle portion.

35. A lens cartridge according to claim 33, wherein said at least one groove ends before said nozzle portion.

36. A lens cartridge according to claim 32, wherein said at least one groove is a set of opposed grooves extending along at least a portion of the length of said passageway.

37. A lens ridge according to claim 32, wherein said at least one groove varies in depth between said lens holding portion and said nozzle portion.

38. A lens cartridge according to claim 32, wherein said passageway is continuous.

39. A lens cartridge according to claim 36, wherein said set of opposed grooves are located above a horizontal centerplane of said passageway.

40. A lens cartridge according to claim 36, wherein said set of opposed grooves are provided adjacent to each other.

41. A lens cartridge according to claim 39, wherein said set of opposed grooves are provided adjacent to each other.

42. A lens cartridge according to claim 32, wherein at least a portion of said passageway tapers inwardly in a direction of insertion of the deformable intraocular lens.

43. A lens cartridge according to claim 42, wherein said inwardly tapering portion of said passageway is located in said nozzle portion.

44. A lens cartridge according to claim 42, wherein said nozzle portion includes a beveled end for facilitating entry of the nozzle portion through an incision in ocular tissue.

45. A lens cartridge according to claim 32, wherein the lens cartridge is made of disposable surgically acceptable plastic.

46. A lens cadge according to claim 32, wherein a cross section of said nozzle portion is one selected from the group of circular and oval.

47. A lens cartridge according to claim 32, wherein a tip of said nozzle portion is provided with slots for allowing expansion of said passageway.

48. A lens cartridge according to claim 32, wherein said lens holding portion and said nozzle portion have a one-piece construction.

49. A lens cartridge according to claim 33, wherein at least a portion of said passageway tapers inwardly in a direction of insertion of the deformable intraocular lens.

50. A lens cartridge according to claim 49, wherein said inwardly tapering portion of said passageway is located in said nozzle portion.

51. A lens cartridge according to claim 34, wherein at least a portion of said passageway tapers inwardly in a direction of insertion of the deformable intraocular lens.

52. A lens cartridge according to claim 51, wherein said inwardly tapering portion of said passageway is located in said nozzle portion.

53. A lens cartridge according to claim 35, wherein at least a portion of said passageway tapers inwardly in a direction of insertion of the deformable intraocular lens.

54. A lens cartridge according to claim 53, wherein said inwardly tapering portion of said passageway is located in said nozzle portion.

55. A lens cartridge according to claim 36, wherein at least a portion of said passageway tapers inwardly in a direction of insertion of the deformable intraocular lens.

56. A lens cartridge according to claim 55, wherein said inwardly tapering portion of said passageway is located in said nozzle portion.

57. A lens cartridge for use with a surgical device having a lens cartridge receiver for implantation of a deformable intraocular lens into an eye through a relatively small incision in the ocular tissue, said lens cartridge comprising:
 a hingeless lens holding portion;
 a nozzle potion connected to and extending from said lens holding portion, said lens holding portion and said nozzle portion having an inwardly tapering passageway of decreasing cross-sectional size extending therethrough for further folding or compressing the deformable intraocular lens when moving through said inwardly tapering passageway; and
 an alignment device defining a portion of the lens cartridge for aligning the lens cartridge in the lens cartridge receiver of the surgical device,
 wherein the lens cartridge is configured to be removably accommodated and positively locked in the lens cartridge receiver of the surgical device, and a tip of said nozzle portion is inserted through a relatively small incision in ocular tissue for implantation of the deformable intraocular lens into an eye.

58. A lens cartridge according to claim 57, wherein said inwardly tapering passageway portion is located in said nozzle portion.

59. A lens cartridge according to claim 57, wherein said passageway is provided with at least one groove extending along at least a portion of the length of said passageway.

60. A lens cartridge according to claim 59, wherein said at least one groove is located in a portion of said passageway extending through said lens holding portion of the lens cartridge.

61. A lens cartridge according to claim 60, wherein said portion of said passageway having said at least one groove transitions to a groove-less portion of said passageway extending through said nozzle portion.

62. A lens cartridge according to claim 60, wherein said at least one groove ends before said nozzle portion.

63. A lens cartridge according to claim 59, wherein said at least one groove is a set of opposed grooves extending along at least a portion of the length of said passageway.

64. A lens cartridge according to claim 59, wherein said at least one groove varies in depth in a direction along the length of said passageway.

65. A lens cartridge according to claim 59, wherein said passageway is continuous.

66. A lens cartridge according to claim 57, wherein said passageway is provided with at least one groove extending along at least a portion of the length of said passageway.

67. A lens cartridge according to claim 66, wherein said at least one groove is located in a portion of said passageway extending through said lens holding portion of the lens cartridge.

68. A lens cartridge according to claim 59, wherein said at least one groove is configured for further folding the deformable intraocular lens when moving through said passageway.

69. A lens cartridge according to claim 68, wherein said at least one groove is configured for further folding the deformable intraocular lens when moving through said passageway.

70. A lens cartridge for use with a surgical device having a lens cartridge receiver for manipulation of a deformable intraocular lens into an eye through a relatively small incision made in the ocular tissue, said lens cartridge comprising:

a hingeless lens holding portion;

a nozzle portion connected to and extending from said lens holding portion, said lens holding potion and said nozzle portion having a passageway extending therethrough, said passageway having at least one inwardly tapering groove for folding the deformable intraocular lens; and an alignment device defining a portion of the lens bridge for aligning the lens cartridge in the lens cartridge receiver of the surgical device, wherein the lens cartridge receiver is configured to be removably accommodated and positively locked in the lens cartridge receiver of the surgical device, and a tip of said nozzle portion is inserted through a relatively small incision in ocular issue for implantation of the deformable intraocular lens into an eye.

71. A lens cartridge according to claim 70, wherein said at least one inwardly tapering groove is located in a portion of said passageway extending through said lens holding portion.

72. A lens cartridge according to claim 71, wherein said portion of said passageway having said at least one groove transitions to a groove-less portion of said passageway extending through said nozzle portion.

73. A lens cartridge according to claim 70, wherein said at least one inwardly tapering groove is a set of opposed inwardly tapering grooves extending along at least a portion of the length of said passageway for continuously folding edges of the deformable intraocular lens inwardly.

74. A lens cartridge according to claim 70, wherein said inwardly tapering passageway portion is located in said nozzle portion.

75. A lens cartridge according to claim 70, wherein said alignment device is located on said lens holding portion.

76. A lens cartridge according to claim 75, wherein said alignment device comprises an extension protruding outwardly from said lens holding portion.

77. A lens cartridge according to claim 76, wherein said extension has a rectangular side profile and a constant thickness along its length.

\* \* \* \* \*